United States Patent
Motoyama

(10) Patent No.: US 8,507,058 B2
(45) Date of Patent: Aug. 13, 2013

(54) SENSOR BUFFER COVER FOR DIGITAL X-RAY IMAGER

(75) Inventor: Osamu Motoyama, Tokyo (JP)

(73) Assignee: Merio Co., Ltd., Tokyo (JP)

( * ) Notice: Subject to any disclaimer, the term of this patent is extended or adjusted under 35 U.S.C. 154(b) by 0 days.

(21) Appl. No.: 12/919,042

(22) PCT Filed: Jun. 29, 2009

(86) PCT No.: PCT/JP2009/002985
§ 371 (c)(1), (2), (4) Date: Oct. 1, 2010

(87) PCT Pub. No.: WO2010/032353
PCT Pub. Date: Mar. 25, 2010

(65) Prior Publication Data
US 2011/0017619 A1  Jan. 27, 2011

(30) Foreign Application Priority Data
Sep. 17, 2008 (JP) ................. 2008-237372

(51) Int. Cl.
*B32B 1/02* (2006.01)
*A61B 6/14* (2006.01)
*G03B 42/04* (2006.01)

(52) U.S. Cl.
USPC .......... 428/35.2; 428/35.7; 378/168; 378/184

(58) Field of Classification Search
USPC ................ 428/35.2, 35.7; 378/168, 184
See application file for complete search history.

(56) References Cited

U.S. PATENT DOCUMENTS

| | | | | |
|---|---|---|---|---|
| 4,653,640 A * | 3/1987 | Akao | ............ | 206/455 |
| 6,062,730 A * | 5/2000 | Sims et al. | ............ | 378/168 |
| 6,520,676 B1 * | 2/2003 | Schmitz | ............ | 378/191 |
| 7,972,060 B2 | 7/2011 | Guichard et al. | | |
| 2005/0259791 A1 * | 11/2005 | Strong | ............ | 378/168 |
| 2006/0098788 A1 * | 5/2006 | McGovern et al. | ............ | 378/169 |
| 2007/0025523 A1 | 2/2007 | Halevi | | |

FOREIGN PATENT DOCUMENTS

| | | |
|---|---|---|
| JP | 1-90507 U | 6/1989 |
| JP | 2004 121846 | 4/2004 |
| JP | 3134839 U | 8/2007 |
| WO | 2008 093501 A1 | 8/2008 |

* cited by examiner

*Primary Examiner* — Erik Kashnikow
(74) *Attorney, Agent, or Firm* — Thomas R. FitzGerald, Esq.; Jason R. Womer, Esq.; Hiscock & Barclay, LLP

(57) ABSTRACT

A sensor buffer cover is provided that is easily held at a fixed position without pain or discomfort to a patient to enable high-definition imaging. It is a sensor buffer cover wherein a cover body constituted as a flexible bag body into which a sensor unit is inserted comprises an inner bag-like sheet made of resin and formed in a rectangular shape to have an opening at one end in the longitudinal direction and an outer sheath member at the base of the inner bag-like sheet constituted as a flexible bag body formed in approximately the same shape as the sensor unit, which covers the periphery of the sensor unit inserted therein and is open at one end in the longitudinal direction, the outer peripheral edge of the base of the inner bag-like sheet and the outer peripheral edge of the outer sheath member covering the base of the inner bag-like sheet being fusion-bonded on three sides to leave an opening and obtain a double bag-like structure.

13 Claims, 2 Drawing Sheets

SENSOR BUFFER COVER FOR DIGITAL X-RAY IMAGER

CROSS-REFERENCE TO RELATED APPLICATIONS

This application is a 371 filing of PCT Application No. PCT/JP2009/002985 filed Jun. 29, 2009, which claims priority to Japanese Patent Application Number 2008-237372 filed Sep. 17, 2008. Reference is made to Japanese Patent Application No. JP 2009-534956 now issued as Japanese Patent No. 4,491,625 which contains the allowable/patentable claims, and which claims internal priority to Japanese Patent Application No. 2008-237372, filed Sep. 17, 2008, the specifications of which are hereby incorporated by reference in their entirety.

TECHNICAL FIELD

This invention relates to a sensor buffer cover for improving intraoral X-ray imaging and diagnosis in dental X-ray imaging.

BACKGROUND ART

In recent years, advances in computer technology have led to the development of digitation technologies also in the field of diagnostic imaging. X-ray imaging (roentgenography) is also performed for ascertaining dental condition in dental treatment, and in this includes panoramic imaging for imaging overall dentition and digital imaging for imaging part of the dentition. In digital imaging, an X-ray film is inserted into the patient's oral cavity, X-rays are directed from outside the patient through the teeth onto a CT or X-ray film, the X-ray film on which teeth were imaged is thereafter developed, converted to digital with a scanner or the like, taken into a computer, and displayed on the screen to observe the imaged X-ray image of the teeth.

In digital imaging for imaging part of the dentition, the sensor of an X-ray imager is inserted directly into the oral cavity, X-rays are directed from outside the patient through the teeth to take the tooth image data directly into a computer and display it to observe an X-ray image of the imaged tooth or teeth.

This digital imaging immediately offers speed and accuracy of examination and treatment and simultaneously enables acquisition of data for highly accurate diagnosis and treatment. Moreover, there are also advantages from the fact that the data is easy to process and analyse, that a method not using X-ray film can be adopted, and, in addition, that X-ray exposure can be markedly reduced.

A CCD (charged coupled device) sensor or CMOS (complementary metal oxide semiconductor) sensor is ordinarily used as the sensor of the intraoral digital X-ray imager, but for obtaining an accurate image of the periodontium, including the root, and the crown, it is necessary to perform imaging with the front of the sensor positioned and fixed vertically in close contact with these portions.

Owing to the need to capture an imaged region of the largest size and highest definition possible, the sensor of the intraoral digital X-ray imager and the periapical region and bitewing region must be accurately brought into close proximity. On the other hand, a sensor unit is inserted into the oral cavity of the patient, so that the cooperation of the patient must be obtained to open the mouth widely around the sensor and maintain a stationary condition. It is therefore necessary for the utilized instruments and the like to have shapes and material properties that do not cause distress. This is particularly important in cases where the patient overreacts to discomfort or tends to experience irritation inside the mouth.

Although dental imaging, which typifies X-ray imaging in dentistry, is utilized at high frequency, it was only recently digitized, and owing to the fact that a film is placed in the oral cavity as mentioned above, it involves issues that hamper widespread use, not only in the mechanical technical aspects related to imaging but also in the points of the environment making film fixing difficult and of the cooperation of the patient being hard to obtain.

In intraoral digital X-ray imaging, the positioning of the imager sensor and of the tooth periapical region and bitewing region is important, but there is a problem in that a high-definition image of the desired region cannot be captured unless patient distress and discomfort are eliminated to the utmost possible.

The sensor of the intraoral digital X-ray imager is inserted into the oral cavities of many patients for use. In order to prevent infection, a thin sheet-like vinyl or thin sheet-like foam soft resin is utilized as a cover that is disposably used and treated. However, intraoral digital X-ray imager sensors are often made of a hard resin or metal, material, so that with the conventional thin sheet-like cover, it is found, among other problems, that the patient is made to feel distress or discomfort because when the sensor is inserted into the patient's oral cavity and brought into close contact with the dentition, its corners strike against the patient's teeth, gums and other tissue, and the sheet is slippery, which makes placement very difficult and accurate imaging hard to achieve.

Although the instruments have been enhanced in performance and reduced in size, the hard imaging sensor is inserted into the irregularly shaped oral cavity, so that patient complaints of discomfort are frequent, while adoption of the intraoral digital system has not spread widely owing to the difficulty of imaging, and there are cases in which a purchaser of a recent sensor nevertheless hesitates to use it. Although technologies have been developed with consideration to ease and convenience of imaging and prevention of infection, many issues remain with regard to sensors and imaging methods that reflect the patient's viewpoint.

In order to overcome these problems, the idea emerged of covering the sensor itself with a flexible buffer means, and the method of covering it with a thin sheet of vinyl or the like that can be used disposably has been adopted. While this method mitigates the distress from insertion of a hard sensor into the oral cavity, a desire has been felt for the development of a buffer that overcomes such drawbacks as that the fitting of the buffer means on the sensor is troublesome and the fitting of a cover separate from the buffer means takes time, and that the buffer means increases the size of the sensor, making it difficult to eliminate the unnatural feel and sense of discomfort toward insertion into the oral cavity.

PRIOR ART DOCUMENTS

Patent Documents

Patent Document 1:
Japanese Patent Publication (A) No. 2004-121846
Patent Document 2
International Publication WO2008/093501

DISCLOSURE OF THE INVENTION

Problem to be Overcome by the Invention

In order to overcome the foregoing problems, the present invention provides a sensor buffer cover for solving them simultaneously and has as its object to provide a sensor buffer cover which imparts an X-ray image capturing sensor cover with flexibility and patient-friendliness, enables replaceability (or disposability), and takes sanitary concerns into consideration, thereby providing a sensor buffer cover enabling a good cooperative relationship with the patient. Another object is to provide a sensor buffer cover having anti-slip property for enabling capture of a high-definition image when the sensor is inserted into the patient's oral cavity.

Means for Solving the Problem

In the sensor buffer cover of the present invention for achieving the foregoing objects, a cover body constituted as a flexible bag body into which a sensor unit is inserted comprises an inner bag-like sheet made of resin and formed in a rectangular shape to have an opening at one end in the longitudinal direction and an outer sheath member at the base of the inner bag-like sheet constituted as a flexible bag body formed in approximately the same shape as the sensor unit, which covers the periphery of the sensor unit inserted therein and is open at one end in the longitudinal direction, the outer peripheral edge of the base of the inner bag-like sheet and the outer peripheral edge of the outer sheath member covering the base of the inner bag-like sheet being fusion-bonded on three sides to leave an opening and obtain a double bag-like structure.

Moreover, the outer surface of the outer sheath member is of a material having patient-friendliness and flexibility. In addition, the outer surface of the outer sheath member is of a material with anti-slip property constituted of sponge, non-woven fabric or the like.

Further, the sensor buffer cover is water resistant or has been subjected to waterproofing treatment, and is structured to be disposable and discarded after a single use.

Moreover, the inner bag-like sheet is an anti-slip sheet whose inner surface is formed with a matte finish. And the inner bag-like sheet can also be a sheet of embossed vinyl chloride resin or polyethylene. In addition, the sensor buffer cover is structured so that the front and back of the outer sheath member and/or the inner bag-like sheet differ in length.

Effects of the Invention

The sensor buffer cover according to the present invention is configured in the foregoing manner and has the following effects.

(1) When inserted into the patient's oral cavity, the sensor buffer cover can be fixed in place without provoking discomfort or an unnatural feeling in the patient, and a high-definition image can be readily captured. Since the inner bag-like sheet and the outer sheath member are integral, sensor insertion is smooth and use is easy. Moreover, the rectangular shape makes manufacture easy, and the structure facilitates insertion of same-type sensors.

(2) As the sensor buffer cover is flexible, it can protect the sensor by absorbing impacts received from the outside when the sensor is bitten by the patient or strikes against the teeth during imaging, or when it is dropped. And since it is flexible and also patient-friendly, its configuration is such as not to provoke discomfort in the patient when the sensor contacts the dentition. Suitable X-ray imaging matched to the condition and shape of the oral cavity of, for example, a child or elderly person is possible.

(3) Pain and discomfort to the patient can be prevented and the sensor can be stably fixed at a suitable location, so that an effect of accurate diagnosis can be anticipated.

(4) X-ray imaging can be performed in a sanitary manner, the cover is disposable, and repeated use without damaging the sensor unit is possible over a long period.

(5) The surface of the inner bag-like sheet is formed with a matte finish to be slip-resistant, whereby reliable imaging can be performed painlessly without using special auxiliary instruments, and with no shift of the sensor unit position during X-ray imaging in either the oral cavity or the inner bag-like sheet.

(6) Use of vinyl chloride resin or polyethylene enables realization of a buffer cover that is high in safety and low in cost.

(7) As the lengths of the outer sheath member and the inner bag-like sheet differ between the front and back of the sensor buffer cover, the imaging face and the non-imaging face can be easily distinguished at the time of sensor insertion.

BEST MODE FOR WORKING THE INVENTION

The sensor buffer cover according to the present invention will be explained in detail based on embodiments shown in the drawings. FIG. 1 is a perspective view of a sensor buffer cover according to the present invention, FIG. 2 is perspective view showing the sensor buffer cover of the present invention fitted on a sensor, FIG. 3 is a perspective view of another embodiment of the sensor buffer cover according to the present invention, and FIG. 4 shows an example of use of the sensor buffer cover according to the present invention.

The sensor buffer cover 10 comprises an inner bag-like sheet 20 and an outer sheath member 30, and is formed to enclose a sensor 50 used in an intraoral imager for digital X-ray imaging.

The sensor buffer cover 10 is a bag-like cover body for internally accommodating the sensor unit of the intraoral X-ray imager and is formed of a flexible material.

The inner bag-like sheet 20 is a bag body formed in a substantially rectangular shape. It is structured for insertion of the sensor 50 into the bag-like interior.

As shown in FIG. 1, it has an opening 22 on one side at one end in the longitudinal direction and is structured for insertion of the sensor 50 through the opening. The inner bag-like sheet 20 is a bag body obtained by adhering two sheets and the three sides other than the opening 22 are joined. In this embodiment, they are adhered by welding using heat treatment, and they must be securely adhered to make the interior waterproof when the sensor 50 is inserted. Moreover, insertion of the sensor 50 can be facilitated by a structure that enlarges the opening 22 by not adhering part of the sides near the opening 22.

The inner bag-like sheet 20 is made of polyethylene, polypropylene, vinyl chloride or other resin material. A polyurethane sheet is used in this embodiment. The adoption of a resin sheet makes the interior of the sheet smooth, so that the sensor 50 is easy to insert in the inner bag-like sheet 20 and can also be smoothly extracted.

Moreover, the width of the inner bag-like sheet 20 is formed to match or be somewhat larger than the width of the sensor 50. By making the width of the sensor 50 about the same, the inner bag-like sheet 20 does not become too large compared to the sensor 50, so that upon fitting in the oral cavity, the sensor 50 does not move inside the sensor buffer cover 10, thereby preventing situations in which high-definition imaging becomes impossible.

In addition, the inner bag-like sheet 20 can be configured so that at least its inside surface is formed with matte-like irregularities. By being made matte-like, it acquires anti-slip property, whereby shifting of the sensor unit inside the inner bag-like sheet can be prevented. Owing to the inner bag-like sheet 20 being imparted with anti-slip property, the sensor 50 does not move internally during use to irritate the inside of the mouth even if the sensor buffer cover 10 is formed larger than the sensor 50, so that the affected part can be reliably and appropriately imaged, and since the size of the sensor buffer cover 10 has extra room relative to the sensor 50, the structure allows easy insertion and extraction of the sensor 50. Since some amount of size allowance is imparted, sensors that differ somewhat in size between manufacturers can also be accommodated. Even with just a single format, it is possible to cope with various types of units, so that the number of sheet types can be reduced and cost minimized to realize good economy.

The anti-slip treatment can be performed by embossing a resin material such as polyethylene, vinyl chloride, polypropylene or the like. Embossing can readily impart anti-slip property at reduced cost.

The outer sheath member 30 is formed by joining two somewhat thick elastic sheet-like bodies matched to the shape of the sensor 50. As shown in FIGS. 1 and 2, it is joined to the inner bag-like sheet 20 so as to enclose the periphery of the base 24 of the inner bag-like sheet 20 into which the sensor 50 is inserted. In this embodiment, one side 32 in the longitudinal direction of the outer sheath member 30 is also open. The outer sheath member 30 covers the base of the inner bag-like sheet 20, and the outer peripheral edge 34 of the outer sheath member is fusion-bonded to the periphery of the base 24 of the inner bag-like sheet. The joining of outer sheath member 30 and inner bag-like sheet 20 gives the sensor holder region of the sensor buffer cover 10 a double bag-like structure.

Although the outer sheath member 30 is formed in a generally rectangular shape matched to the shape of the sensor unit in the present embodiment, it is not limited to a rectangular shape and can be made into a generally elliptical outer sheath member by rounding the corners in line with the sensor shape. The rounding of the corners has the effect of making intromission easier for the patient and enables enhancement of patient comfort. Moreover, as shown in FIG. 3, the side 32 can be slightly widened at the opposite extremities to facilitate insertion of the sensor 50.

The outer surface of the outer sheath member 30 is formed of a patient-friendly and flexible material. As the region contacted is in the oral cavity, this improves insertability and comfort and has the effect of minimizing discomfort during use. Patient-friendliness and flexibility can be imparted by using a somewhat thick material of, for example, resin, silicone, synthetic rubber, sponge, nonwoven fabric or the like.

Slipping can be prevented and image quality enhanced by using sponge, nonwoven fabric or other anti-slip material for the outer surface of the outer sheath member 30. The oral cavity may be full of saliva, the sensor may easily move or shift owing to the projections and depressions in the oral cavity, and the condition is slippery and makes fixing at a suitable location difficult, but this problem can be overcome by using an anti-slip material. In conventional embodiments only vinyl sheet was used, so that even when the sensor was covered for use, it was still very slippery owing to the saliva and the like inside the mouth, making it difficult to fix in place only by gentle pressing.

In the case of a foam material, a slippery film occurs on the surface, so that for obtaining anti-slip property, it is preferable when foaming the material to use one in a film-free condition during processing. In addition, since one whose foamed bubbles are fine is slippery even if the film is removed, urethane, NBR synthetic rubber or other material with relatively coarse bubbles is preferable. Moreover, two thinly sliced sheets of a material produced by foaming and having a thickness of 0.5 mm to 4 mm, more preferably a thickness of 1 mm to 2 mm, are preferably joined and formed. Use of thin sheet enables comfortable imaging without an unnatural feeling due to thickness. And by imparting a certain degree of thickness, an effect of enhancing impact absorption can be anticipated.

In this embodiment, urethane material is used for the outer sheath member 30, and thanks to the affinity with the inner bag-like sheet 20 formed of similar polyurethane sheet, firm fusion-bonding is realized. Moreover, as another embodiment, it is possible to adopt a structure wherein an inner bag-like sheet 20 of vinyl chloride resin is fusion-bonded to the outer sheath member 30 of polyurethane. In addition, there is preferably fusion bonded a sheet obtained by subjecting the inner bag-like sheet 20 to embossing as an anti-slip treatment.

The outer sheath member 30 and inner bag-like sheet 20 can be structured to differ in longitudinal length between the front and back. By making one of the two sheets overlaid and bonded at the periphery longer, the front and back are easy to distinguish when the sensor 50 is inserted. And it is also possible to adopt a structure in which one side of one or the other of the outer sheath member 30 and inner bag-like sheet 20 is formed long. The difference in the length of the inner bag-like sheet 20 and/or inner bag-like sheet 20 makes it possible to avoid misidentification of the sensor imaging side.

The sensor buffer cover 10 with the sensor 50 inserted is shown in FIG. 1.

The sensor 50 is a small dental image pickup unit and can, for example, be a CMOS, CCD or film-like. A lead line 52 is installed to extend from the sensor 50 and transmits image data obtained by the sensor 50 to an external computer.

In this embodiment, since the sensor buffer cover 10 is to be discarded after a single use (is disposable), it can maintain sanitation. Patients can be protected from infection because the sensor buffer cover 10 is made to be replaceable after a single use.

As shown in FIG. 4, the sensor buffer cover 10 of the present invention encloses the sensor 50 and is inserted into the oral cavity of the patient for use.

In order to protect the sensor 50, the present embodiment is also configured to provide water resistance for the sensor inside. For example, use of a disposable and inexpensive water-resistant film for the inner bag-like sheet 20 is sanitary and also enables cost reduction. In the present embodiment, use of the water-resistant polyurethane sheet for the inner bag-like sheet 20 makes the structure water-resistant. And still more thorough water resistance can be obtained by also subjecting the outer sheath member 30 to waterproofing treatment.

In the sensor buffer cover 10 of the present invention, the inner bag-like sheet and the outer sheath member 30 exhibit anti-slip property, so that simple and appropriate imaging can be performed without use of auxiliary tools for positioning or positional fixing. And it is a low-cost buffer cover that is suitable for disposable use, while also possessing anti-slip property and water-resistance.

Moreover, in the present embodiment manufacture is easy and manufacturing cost can be reduced because the inner bag-like sheet 20 and outer sheath member 30 are formed in the ordinary rectangular shape seen heretofore. While the configuration of the present embodiment fusion-bonds the inner bag-like sheet 20 and outer sheath member 30 at the portions of their outer peripheral edges other than the opening regions, a configuration is also possible that joins not only the outer peripheral edges but also the outer surface of the inner bag-like sheet and the inner surface of the outer sheath member.

In addition, in the present invention, the forming of the inner bag-like sheet 20 in a long rectangular shape enables protection of the lead line 52 of the sensor 50, facilitates insertion, and provides a sensor buffer cover that is also excellent in terms of sanitation as regards the sensor unit inserted into the mouth. Another advantage is that the sensor 50 is easy to insert because from the opening 22 to the base 24 is formed to substantially the same width. Furthermore, it is possible to adopt a structure wherein a necked section is provided locally in the longitudinal direction so that the inserted sensor does not readily come out of the opening during use.

Moreover, cost can be reduced by using a patient-friendly and flexible material for only the outer sheath member 30 that covers the sensor 50.

EXPLANATION OF SYMBOLS

Figure 1:
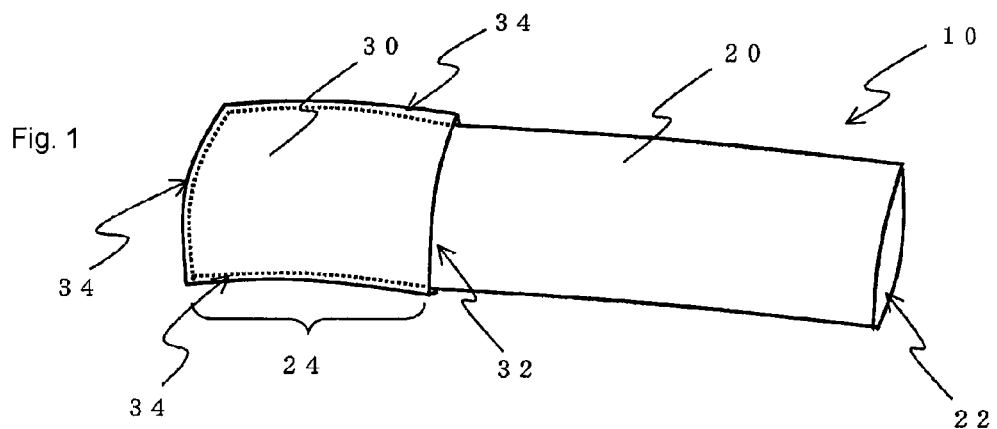
FIG. 1 is a perspective view of a sensor buffer cover according to the present invention.
Figure 2:
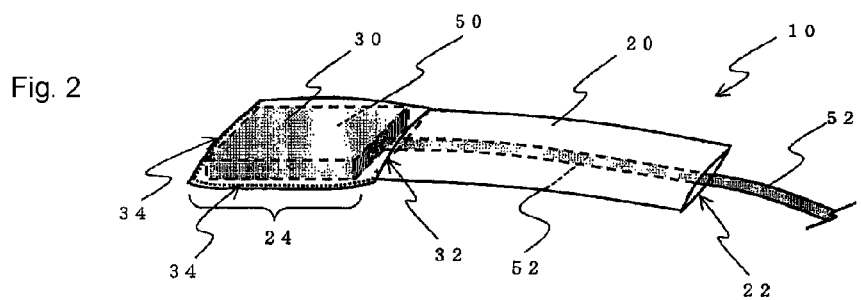
FIG. 2 is perspective view showing the sensor buffer cover of the present invention fitted on a sensor
Figure 3:
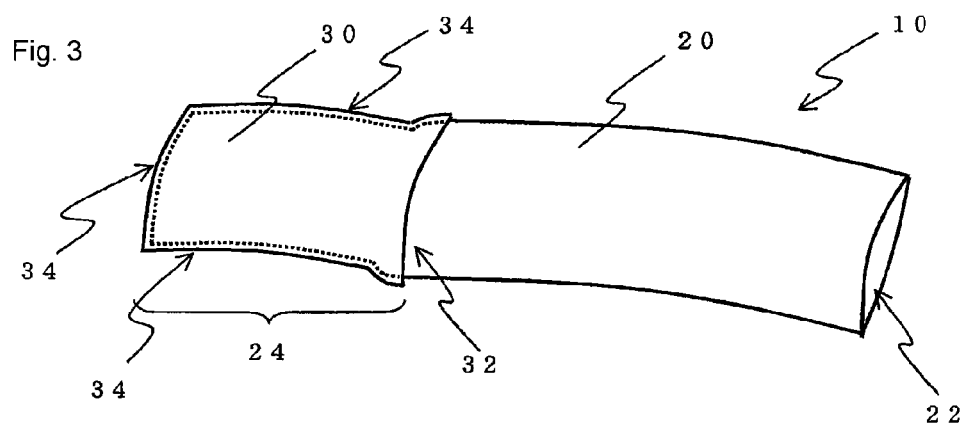
FIG. 3 is a perspective view of another embodiment of the sensor buffer cover according to the present invention.
Figure 4:
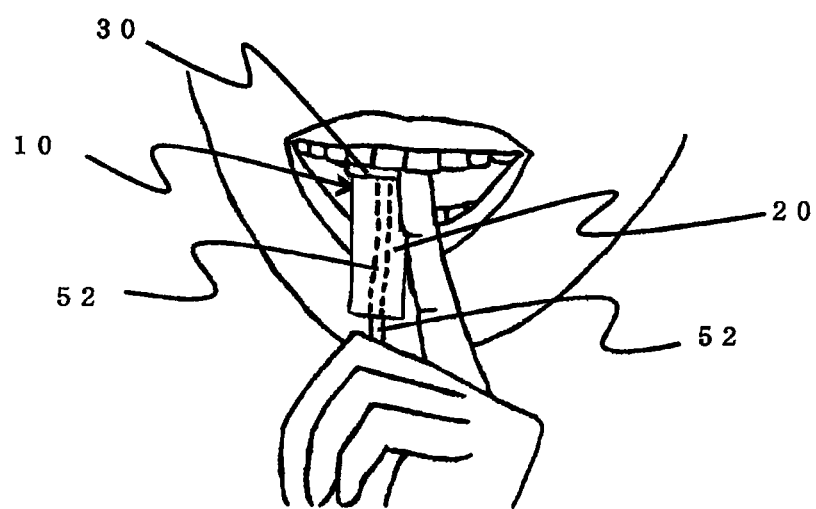
FIG. 4 shows an example of use of the sensor buffer cover according to the present invention.

10 . . . sensor buffer cover, 20 . . . inner bag-like sheet, 22 . . . opening, 24 . . . base, 30 . . . outer sheath member, 32 . . . side, 34 . . . outer peripheral edge, 50 . . . sensor, 52 . . . lead line

The invention claimed is:

1. A sensor buffer cover characterized in that
a cover body transparent to radiation sensible by a sensor and constituted as a flexible bag body into which a sensor unit having a predetermined shape is inserted comprises:
an inner bag made of resin and formed in a rectangular shape being joined on three sides and having an opening at one end in the longitudinal direction and a base at the opposite end; and
an outer sheath member at the base of the inner bag constituted as a flexible bag body formed in approximately the same predetermined shape as the sensor unit, which covers the periphery of the sensor unit inserted therein and is open at one end in the longitudinal direction,
the outer sheath member covering the base of the inner bag and being fusion-bonded along the outer peripheral edge of the base of the inner bag on three sides to leave an opening in the longitudinal direction and obtain a double bag structure for receiving a sensor in the inner bag.

2. A sensor buffer cover of claim 1, characterized in that the outer surface of the outer sheath member is a flexible material selected from the group consisting of: resin, silicone, synthetic rubber, sponge and nonwoven fabric.

3. A sensor buffer cover of claim 1, characterized in that the outer surface of the outer sheath member is of a material with anti-slip property.

4. A sensor buffer cover of any of claims 1 to 3, characterized in that the sensor buffer cover is water resistant or has been subjected to waterproofing treatment.

5. A sensor buffer cover of claim 1, characterized in that the inner bag-like sheet is an anti-slip sheet whose inner surface is formed with a matte finish.

6. A sensor buffer cover of claim 1, characterized in that the inner bag-like sheet is a sheet of embossed vinyl chloride resin or polyethylene.

7. A sensor buffer cover of claim 1, characterized in that the sensor buffer cover differs in the length of the outer sheath member and/or the inner bag-like sheet between the front and the back.

8. A sensor buffer cover of claim 1, characterized in that the inner bag-like sheet has a longitudinal length that is longer between the front and the back than a longitudinal length of the outer sheath member.

9. A sensor buffer of claim 1 wherein the inner bag and the outer sheath are transparent to X-rays.

10. A sensor buffer of claim 1 wherein the inner bag has a width matching or slightly larger than the width of the sensor for preventing a sensor inserted into the inner bag from moving inside the inner bag.

11. A sensor buffer cover characterized in that
a cover body transparent to radiation sensible by a sensor and constituted as a flexible bag body into which a sensor unit is inserted comprises:
a first generally rectangular-shaped bag made of resin being joined on three sides and having one opening at an end in the longitudinal direction; and
a second generally rectangular-shaped bag being approximately the same shape as the sensor unit, said second generally rectangular-shaped bag having a width that is approximately the same as a width of said first generally rectangular-shaped bag and having a longitudinal length that is shorter than a longitudinal length of said first generally rectangular-shaped bag;
said second generally rectangular-shaped bag covering a portion of said first generally rectangular-shaped bag and being fusion-bonded on three sides of the outer peripheral edge forming a double bag-like structure leaving an opening in the longitudinal direction and in which the longitudinal length of said first generally rectangular-shaped bag extends beyond the longitudinal length of said second generally rectangular-shaped bag for receiving a sensor in the first rectangular shaped bag.

12. A sensor buffer of claim 11 wherein the first and second bags are transparent to X-rays.

13. A sensor buffer of claim 11 wherein the inner bag has a width matching or slightly larger than the width of the sensor for preventing a sensor inserted into the inner bag from moving inside the inner bag.

\* \* \* \* \*